United States Patent [19]

Cricchio

[11] 4,129,562

[45] Dec. 12, 1978

[54] THIAZOLO-RIFAMYCIN DERIVATIVES AND A METHOD FOR THEIR PREPARATION

[75] Inventor: Renato Cricchio, Varese, Italy

[73] Assignee: Gruppo Lepetit S.p.A., Milan, Italy

[21] Appl. No.: 796,291

[22] Filed: May 12, 1977

[30] Foreign Application Priority Data

May 28, 1976 [GB] United Kingdom ............... 22205/76

[51] Int. Cl.² ........................................ C07D 513/18
[52] U.S. Cl. ............................. 260/239.3 P; 424/270; 424/244; 424/267; 424/248.51; 424/250
[58] Field of Search ................................... 260/239.3 P

[56] References Cited

U.S. PATENT DOCUMENTS 4,042,683  8/1977  White et al. ..................... 424/117

FOREIGN PATENT DOCUMENTS 832921   12/1975  Belgium ........................... 260/239.3 P
2537902  3/1976   Fed. Rep. of Germany ... 260/239.3 P
482716   1/1970   Switzerland ..................... 260/239.3 P Primary Examiner—Henry R. Jiles
Assistant Examiner—Robert T. Bond
Attorney, Agent, or Firm—James W. Ambrosius

[57] ABSTRACT

Novel 4-desoxy-thiazolo[5,4-c]rifamycin SV derivatives having antibacterial activity and a method of preparing same by the reaction of rifamycin S with a cysteine derivative followed by the oxidation of the resulting product.

10 Claims, No Drawings

THIAZOLO-RIFAMYCIN DERIVATIVES AND A METHOD FOR THEIR PREPARATION

SUMMARY OF THE INVENTION

The present invention relates to novel derivatives of rifamycin and to a process for their preparation. More particularly the compounds that are the subject of the present invention are 4-desoxy-thiazolo[5,4-c]rifamycin SV derivatives represented by the general formula:

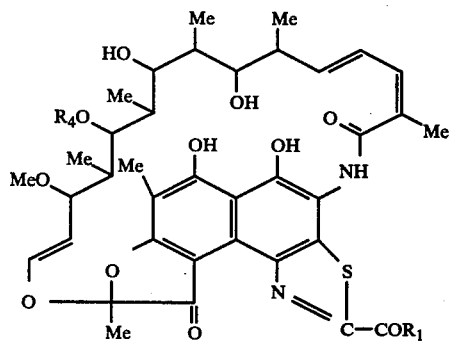

wherein:

$R_1$ represents loweralkoxy, cycloalkoxy, phenoxy, benzoxy, or an amino or hydrazino moiety represented by the formulas: $-NR_2R_3$ and $-NH-NR_2R_3$ wherein $R_2$ and $R_3$ are independently selected from the group consisting of hydrogen, lower alkyl, hydroxy lower alkyl, cycloalkyl, phenyl or benzyl or $R_2$ and $R_3$ taken together with the adjacent nitrogen atom represent a saturated 5 or 6 membered heterocyclic ring which may contain an additional nitrogen or oxygen atom in the ring and may be optionally substituted with zero, one, or two lower alkyl groups and $R_4$ represents hydrogen or acetyl.

As used in the specification and claims the terms "alkyl" and "alkoxy" refer to a branched or linear aliphatic chain having from 1 to about 4 carbon atoms, and the terms "cycloalkyl" and "cycloalkoxy" refer to a moiety containing from 5 to 8 carbon atoms in the saturated ring. In addition, as used herein the terms "phenyl", "phenoxy", "benzyl", and "benzoxy" refer to groups optionally substituted with zero, one, or two substituents independently selected from the group consisting of chloro, bromo, fluoro, nitro, trifluoromethyl, lower alkoxy, cyano, loweralkylsulfonyl and sulfamoyl.

The compounds of the present invention have been found to be active antibacterial agents and to possess relatively low toxicity toward host animals. The compounds have shown satisfactory activity in the control and killing of Gram positive and Gram negative strains of bacteria. For example, at concentrations of from about 0.1 micrograms/ml to 5 micrograms/ml the compounds have been found to effectively inhibit the growth of *Staphylococcus aureus, Streptococcus haemoliticus, Diplococcus pneumoniae,* and *Mycobacterium tuberculosis* $H_{37}Rv$. The above list of organisms is intended to serve as examples and the activity is not to be construed as being limited to these organisms. The novel compounds also inhibit at low concentrations the growth of microorganisms resistant to other known and widely used drugs.

The novel thiazolo-rifamycin derivatives that are the subject of this invention are prepared by reacting rifamycin S or its 25-desacetyl derivative (see formula II below) with a cysteine derivative (see formula III). Said cysteine derivative may be used as a free base or as an acid addition salt thereof, such as for example the corresponding hydrohalide or sulfate and the like. The resulting product is then oxidized to give the compounds of the present invention as represented in formula I above.

The general reaction may be represented as follows:

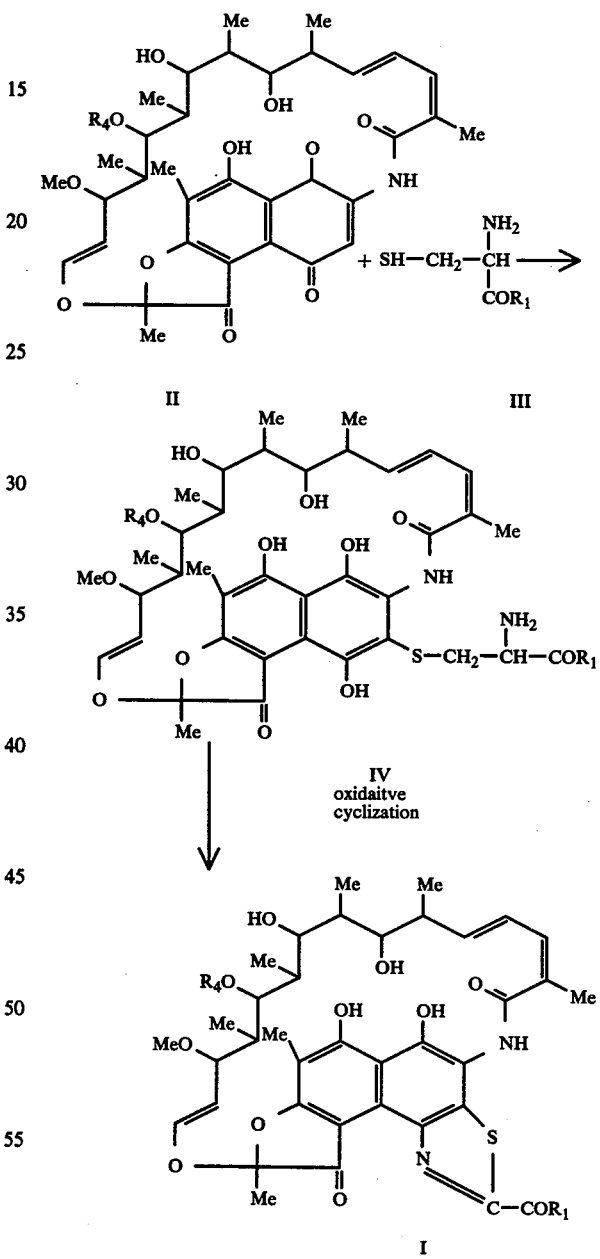

wherein $R_1$ and $R_4$ represent the same moieties as already defined.

The reaction may be carried out by separating the intermediate IV prior to carrying out the oxidative cyclization or directly without isolating the intermediate IV. In carrying out the first step of the above reaction sequence about equimolar proportions of the two reactants II and III are mixed in a water-miscible organic solvent such as for example a lower alkanol, dioxane, tetrahydrofuran and the like.

The temperature of the first step of the reaction may range between room temperature and the boiling temperature of the solvent. The reaction time will depend on the temperature of the reaction and is generally determined by observing the disappearance of rifamycin S by thin layer chromatography. Suitable oxidizing agents for promoting the second step of the reaction can be selected from a wide group of oxidizing agents such as for example, quinones, organic nitrites, peroxides, persulfates, nitrous acid, tetravalent manganese and lead derivatives, trivalent iron derivatives, mercuric and cupric salts and the like. Among the preferred oxidizing agents are p-quinone, 2,5-dimethyl-p-quinone, 2,6-dimethoxy-p-quinone, tetrachloro-p-quinone(chloranil), dichlorodicyano-p-quinone, duroquinone, rifamycin S, alkyl nitrites, hydrogen peroxide, alkali metal persulfates, alkali metal ferricyanides, cupric acetate, mercuric acetate and manganese dioxide.

The second step of the reaction which is defined as "oxidative cyclization" is advantageously carried out at a temperature between about room temperature and the boiling temperature of the reaction mixture, and preferably between about 18° C. and about 45° C. The pH of the reaction mixture containing the oxidizing agent is maintained between 2 and 6.5, preferably between 4 and 5 and most preferably between 4.2 and 4.8.

According to one preferred embodiment of the invention, equimolecular proportions of rifamycin S or its 25-desacetyl derivative and a cysteine derivative of formula III are refluxed for a time ranging from about 15 minutes to 3 hours in a lower alkanol. The intermediate IV, which forms, is contacted with the selected oxidizing agent and the pH of the solution is kept between 4.2 and 4.8 by means of an aqueous buffer system. When the reaction, which is followed by thin layer chromatography, is completed the mixture is worked up in order to eliminate the oxidizing agent or its reaction products. The operative conditions obviously depend on the nature of the selected oxidizing agent. More particularly, when quinones are used as the oxidants, it may be useful to eliminate the resulting hydroquinone derivative by reoxidation to the original quinone and simultaneous extraction of the quinone with a proper solvent. Once the reaction side-products have been eliminated, the thiazolorifamycin of formula I may be easily recovered as a crystalline product by following usual techniques.

Alternatively the reaction outlined above may be carried out without isolating the intermediate. In this case the final product (formula I) is obtained by leaving a solution of the starting compounds II and III in a water-miscible organic solvent at a temperature of from about 18° C. to 45° C. for several hours (generally from about 10 to 80 hours) at a pH ranging between 2 and 6.5, preferably between 4 and 5, and most preferably between 4.2 and 4.8 in the presence of a suitable oxidizing agent which does not unfavorably interfere with the reactants. Oxidizing agents which have been satisfactorily employed in this procedure include the tetrasubstituted quinone and rifamycin S, itself. The course of the reaction is followed by thin layer chromatography showing the disappearance of the starting rifamycin S and the presence of a new yellow fluorescent spot indicating the presence of the thiazolorifamycin of formula I.

The recovery of the end products involves several extraction operations and generally the same procedure used in the two-steps process can be advantageously followed. The starting rifamycin S can be prepared according to the method described in British patent specification No. 924,472 and the reactants of formula III are easily prepared from cysteine by means well known in the art.

Compounds of formula I may also be obtained through chemical modification of other compounds falling within the same formula I prepared according to the reaction scheme outlined before. More precisely compounds of formula I wherein $R_1$ represents a group $-NR_2R_3$ or $-NH-NR_2R_3$ are prepared by reaction of the compounds of formula I wherein R is a group $-OR_1$ with corresponding amines or hydrazines having the formula $HNR_2R_3$ or $H_2N-NR_2R_3$.

The following examples will serve to further illustrate the present invention, but are not to be construed as a limitation thereon.

EXAMPLE 1

4-desoxy-2'-carbomethoxy-thiazolo[5,4-c] rifamycin SV

To a solution containing 7 g of rifamycin S (0.01 mole) in 300 ml of methanol and 20 ml of buffer pH 4.6 (aqueous solution of citric acid and di-sodium phosphate), 0.850 g (0.005 mole) of cysteine methyl ester hydrochloride was added. The solution was left at room temperature until thin layer chromatography revealed the disappearance of rifamycin S. The reaction mixture was then diluted with 1 liter of water and extracted with 500 ml of ethyl acetate. A solution of 6 g of potassium ferricyanide in 500 ml of buffer pH 7.38 was added to the organic phase and the mixture was stirred for a few minutes to oxidize the rifamycin SV to rifamycin S which dissolved into the ethylacetate phase. The buffered solution was separated, acidified with diluted HCl and extracted with ethyl acetate.

From the organic phase, after being washed with water, dried and concentrated to a small volume, 2.4 g of the title product crystallized out. (M.p. 190°–205° C. with decomposition).

| Microanalysis | C | H | N | S |
|---|---|---|---|---|
| Calculated for $C_{40}H_{48}N_2O_{13}S$ | 60.28 | 6.07 | 3.51 | 4.02 |
| found | 60.36 | 6.25 | 3.41 | 3.90 |

U.V. Spectrum (pH 7.38): λ max at 225 mμ ($E_{1\ cm}^{1\%}$ = 573), 295 mμ ($E_{1\ cm}^{1\%}$ = 364) and 394 mμ ($E_{1\ cm}^{1\%}$ = 238).

EXAMPLE 2

4-desoxy-2'-carbamyl-thiazolo[5,4-c]rifamycin SV

The title compound was obtained according to Example 1 from rifamycin S and cysteine amide hydrochloride. (M.p. 210°–240° C. with decomposition).

| Microanalysis | C | H | N | S |
|---|---|---|---|---|
| Calculated for $C_{39}H_{47}N_3O_{12}S$ | 59.91 | 6.06 | 5.37 | 4.10 |
| found | 59.54 | 6.16 | 5.22 | 3.99 |

U.V. Spectrum (pH 7.38): λ max at 225 mμ ($E_{1\ cm}^{1\%}$ = 586), 290 mμ ($E_{1\ cm}^{1\%}$ = 348) and 395 mμ ($E_{1\ cm}^{1\%}$ = 228).

EXAMPLE 3

4-desoxy-2'-(4-methyl-1-piperazinyl)carbonyl-thiazolo[5,4-c]rifamycin Sv 2 g of the compound of Example 1 was dissolved in 50 ml of N-methyl-piperazine. After 30 minutes the reaction mixture was acidified with diluted HCl and extracted with ethyl acetate. From the organic phase, washed with water, dried and concentrated to a small volume, 1.4 g of the title product crystallized out. (M.p. 190° C. with decomposition).

| Microanalysis | C | H | N | S |
|---|---|---|---|---|
| Calculated for $C_{44}H_{56}N_4O_{12}S$ | 61.09 | 6.52 | 6.47 | 3.70 |
| found | 60.98 | 6.69 | 6.42 | 3.60 |

U.V. Spectrum (pH 7.38): λ max at 225 mμ ($E_{1\,cm}^{1\%}$ = 502), 300 mμ ($E_{1\,cm}^{1\%}$ = 325) and 393 mμ ($E_{1\,cm}^{1\%}$ = 197).

By operating according to the procedure of the foregoing example the following compounds are obtained.

EXAMPLE 4

4-desoxy-2'-(morpholino)carbonyl-thiazolo[5,4-c]rifamycin SV

The compound of the title is prepared according to the procedure of Example 3 from the compound of Example 1 and morpholine. (M.p. 162°-166° C. with decomposition).

| Microanalysis | C | H | N | S |
|---|---|---|---|---|
| Calculated for $C_{43}H_{53}N_3O_{13}S$ | 60.62 | 6.27 | 4.93 | 3.76 |
| found | 60.80 | 6.20 | 5.02 | 3.69 |

U.V. Spectrum (pH 7.38): λ max at 225 mμ ($E_{1\,cm}^{1\%}$ = 514), 300 mμ ($E_{1\,cm}^{1\%}$ = 346) and 393 mμ ($E_{1\,cm}^{1\%}$ = 205).

EXAMPLE 5

4-desoxy-2'-(piperidino)carbonyl-thiazolo[5,4-c]rifamycin SV

The compound of the title was prepared according to the procedure of Example 3 from the compound of Example 1 and piperidine (M.p. 175°-178° C. with decomposition).

| Microanalysis | C | H | N | S |
|---|---|---|---|---|
| Calculated for $C_{44}H_{55}N_3O_{12}S$ | 62.17 | 6.52 | 4.94 | 3.77 |
| found | 62.19 | 6.55 | 5.12 | 3.75 |

U.V. Spectrum (pH 7.38): λ max at 225 mμ ($E_{1\,cm}^{1\%}$ = 545), 300 mμ ($E_{1\,cm}^{1\%}$ = 352) and 393 mμ ($E_{1\,cm}^{1\%}$ = 207).

EXAMPLE 6

4-desoxy-2'-[N-ethyl-N-(2-hydroxyethyl)carbamyl]-thiazolo[5,4-c]rifamycin SV The title compound was prepared according to the procedure of Example 3 from the compound of Example 1 and ethyl-ethanol-amine (M.p. 157°-160° C. with decomposition).

| Microanalysis | C | H | N | S |
|---|---|---|---|---|
| Calculated for $C_{43}H_{55}N_3O_{13}S$ | 60.48 | 6.49 | 4.92 | 3.75 |
| found | 59.97 | 6.56 | 5.01 | 3.62 |

U.V. Spectrum (pH 7.38): λ max at 225 mμ ($E_{1\,cm}^{1\%}$ = 516), 300 mμ ($E_{1\,cm}^{1\%}$ = 334) and 393 Mμ ($E_{1\,cm}^{1\%}$ = 202).

EXAMPLE 7

4-desoxy-2'-(methylcarbamyl)thiazolo[5,4-c]rifamycin SV

The title compound was prepared according to the procedure of Example 3 from the compound of Example 1 and methylamine. (M.p. 191°-192° C. with decomposition).

| Microanalysis | C | H | N | S |
|---|---|---|---|---|
| Calculated for $C_{41}H_{51}N_3O_{12}S$ | 60.80 | 6.35 | 5.19 | 3.96 |
| found | 60.69 | 6.25 | 5.10 | 3.91 |

U.V. Spectrum (pH 7.38): λ max at 225 mμ ($E_{1\,cm}^{1\%}$ = 545), 300 mμ ($E_{1\,cm}^{1\%}$ = 342) and 393 mμ ($E_{1\,cm}^{1\%}$ = 212).

EXAMPLE 8

4-desoxy-2'-(cyclohexylcarbamyl)thiazolo[5,4-c]rifamycin SV

The compound of the title was prepared according to the procedure of Example 3 from the compound of Example 1 and cyclohexylamine (M.p. 200°-202° C. with decomposition).

| Microanalysis | C | H | N | S |
|---|---|---|---|---|
| Calculated for $C_{44}H_{57}N_3O_{12}S$ | 62.02 | 6.74 | 4.93 | 3.76 |
| found | 61.97 | 6.61 | 4.81 | 3.74 |

U.V. Spectrum (pH 7.38): λ max at 225 mμ ($E_{1\,cm}^{1\%}$ = 536), 300 mμ ($E_{1\,cm}^{1\%}$ = 343) and 393 mμ ($E_{1\,cm}^{1\%}$ = 211).

EXAMPLE 9

4-desoxy-2'-(2,2-dimethylhydrazinocarbonyl)-thiazolo[5,4-c]rifamycin SV

A solution of 1 gram of 4-desoxy-2'-carbomethoxy-thiazolo[5,4-c]rifamycin SV in 5 cc of dimethylhydrazine was refluxed for 20 minutes, diluted with 100 cc of water and extracted with ethyl acetate. The ethyl acetate extract, was separated and extracted with buffer pH 8. In turn the buffered phase was acidified with diluted HCl and extracted with ethyl acetate. From this organic extract, washed with water, dried and concentrated to a small volume 0.6 g of the compound of the title crystallized out. (M.p. 186-190° C. with decomposition).

| Microanalysis | C | H | N | S |
|---|---|---|---|---|
| Calculated for $C_{41}H_{52}N_4O_{12}S$ | 59.69 | 6.35 | 6.79 | 3.89 |
| found | 58.95 | 6.33 | 6.49 | 3.54 |

U.V. Spectrum (pH 7.38): λ max at 225 mμ ($E_{1\,cm}^{1\%}$ = 519), 258 mμ (shoulder), 300 mμ ($E_{1\,cm}^{1\%}$ = 351), and 393 mμ ($E_{1\,cm}^{1\%}$ = 216).

EXAMPLE 10

4-desoxy-2'-carbomethoxy-thiazolo[5,4-c]rifamycin SV

A solution of 7 g of rifamycin S in 300 ml of methanol was added to 1.8 g of cysteine methyl ester hydrochloride and 1.53 ml of triethylamine and the mixture refluxed for 20 minutes.

The reaction mixture was then poured into water, acidified and extracted with ethyl acetate. From the organic solution, concentrated to a small volume, 6 g of 3-[(2-amino-2-carbomethoxy-ethyl)mercapto]rifamycin SV crystallized out (M.p. > 160° C. with decomposition).

830 mg of this compound was dissolved in 30 ml of methanol, added to 2 ml of buffer pH 4.6 and 230 mg of dichlorodicyano-p-quinone and allowed to stand at room temperature for 15 hours. The reaction mixture was then concentrated to dryness and taken up with chloroform. The insoluble portion is filtered off and the filtrate is added with an aqueous buffer solution at pH 8.04.

The aqueous solution is then separated, acidified and extracted with ethyl acetate. By concentrating this organic solution, 200 mg of the compound of the title crystallized out. (M.p. 189–205° C. with decomposition).

Alternatively the title compound may be obtained by adding the oxidizing agent and the buffer solution directly to the reaction mixture without separating the open-chain intermediate.

EXAMPLE 11

4-desoxy-2'-carbomethoxy-thiazolo[5,4-c]rifamycin SV

The compound of the title is prepared according to the procedures of the foregoing example but using 2,6-dimethyl-p-quinone instead of dichlorodicyano-p-quinone.

EXAMPLE 12

4-desoxy-2'-carbomethoxy-thiazolo[5,4-c]rifamycin SV

The compound of the title is prepared according to the procedure of Example 9 but using tetrachloro-p-quinone instead of dichlorodicyano-p-quinone.

EXAMPLES 13–18

4-desoxy-2'-carbomethoxy-thiazolo[5,4-c]rifamycin SV

The compound of the title is prepared according to the procedure of Example 9 but using, instead of dichlorodicyano-p-quinone, one of the following oxidizing agents:
 anthraquinone
 2,6-dimethoxy-p-quinone
 Manganese dioxide
 Ferric chloride
 Potassium ferricyanide
 2,3,5,6-tetramethyl-p-quinone (duroquinone)

By operating according to the procedure of the foregoing examples the following compounds are obtained:

(1) 4-desoxy-2'-(phenoxycarbonyl)thiazolo[5,4-c]rifamycin SV
(2) 4-desoxy-2'-[(phenylmethoxy)carbonyl]-thiazolo[5,4-c]rifamycin SV
(3) 2'-(cyclopentyloxycarbonyl)-4-desoxy-thiazolo[5,4-c]rifamycin SV
(4) 2'-(cyclohexyloxycarbonyl)-4-desoxy-thiazolo[5,4-c]rifamycin SV
(5) 4-desoxy-2'-[(phenylamino)carbonyl]thiazolo[5,4-c]rifamycin SV
(6) 4-desoxy-2'-[[(phenylmethyl)amino]carbonyl]-thiazolo[5,4-c]rifamycin SV
(7) 4-desoxy-2'-[(diphenylamino)carbonyl]-thiazolo[5,4-c]rifamycin SV
(8) 4-desoxy-2'-[(dimethylamino)carbonyl]-thiazolo[5,4-c]rifamycin SV
(9) 4-desoxy-2'-[(N'-ethylhydrazino)carbonyl]-thiazolo[5,4-c]rifamycin SV
(10) 4-desoxy-2'-[(N'-phenylhydrazino)carbonyl]-thiazolo[5,4-c]rifamycin SV
(11) 4-desoxy-2'-[[N'-(phenylmethyl)hydrazino]carbonyl]thiazolo[5,4-c]rifamycin SV
(12) 4-desoxy-2'-[(N',N'-diphenylhydrazino)carbonyl]thiazolo[5,4-c]rifamycin SV
(13) 2'-[(N'-cyclohexylhydrazino)carbonyl]-4-desoxy-thiazolo[5,4-c]rifamycin SV
(14) 4-desoxy-2'-[[N'-ethyl-N'-(2-hydroxyethyl)hydrazino]carbonyl]thiazolo[5,4-c]rifamycin SV
(15) 4-desoxy-2'-[[(1-piperazinyl)amino]carbonyl]-thiazolo[5,4-c]rifamycin SV
(16) 4-desoxy-2'-[[(4-methyl-1-piperazinyl)amino]carbonyl]thiazolo[5,4-c]rifamycin SV
(17) 4-desoxy-2'-[[(4-morpholinyl)amino]carbonyl]-thiazolo[5,4-c]rifamycin SV
(18) 4-desoxy-2'-[[(1-piperidinyl)amino]carbonyl]-thiazolo[5,4-c]rifamycin SV
(19) 25-desacetyl-4-desoxy-2'-(methoxycarbonyl)-thiazolo[5,4-c]rifamycin SV
(20) 25-desacetyl-4-desoxy-2'-(ethoxycarbonyl)-thiazolo[5,4-c]rifamycin SV
(21) 2'-(aminocarbonyl)-25-desacetyl-4-desoxy-thiazolo[5,4-c]rifamycin SV
(22) 25-desacetyl-4-desoxy-2'-[(methylamino)carbonyl]thiazolo[5,4-c]rifamycin SV
(23) 25-desacetyl-4-desoxy-2'-[[ethyl(2-hydroxyethyl)amino]carbonyl]thiazolo[5,4-c]rifamycin SV
(24) 2-[(cyclohexylamino)carbonyl]-25-desacetyl-4-desoxy-thiazolo[5,4-c]rifamycin SV
(25) 25-desacetyl-4-desoxy-2'-[(1-piperidinyl)carbonyl]thiazolo[5,4-c]rifamycin SV
(26) 25-desacetyl-4-desoxy-2'-[(4-morpholinyl)carbonyl]thiazolo[5,4-c]rifamycin SV
(27) 25-desacetyl-4-desoxy-2'-[(4-methyl-1-piperazinyl)carbonyl]thiazolo[5,4-c]rifamycin SV
(28) 25-desacetyl-4-desoxy-2'-[N',N'-dimethylhydrazino)carbonyl]thiazolo[5,4-c]rifamycin SV
(29) 25-desacetyl-4-desoxy-2'-[(N'-phenylhydrazino)carbonyl]thiazolo[5,4-c]rifamycin SV
(30) 2'-[(N'-cyclohexylhydrazino)carbonyl]-25-desacetyl-4-desoxy-thiazolo[5,4-c]rifamycin SV
(31) 25-desacetyl-4-desoxy-2'-[[(4-methyl-1-piperazinyl)amino]carbonyl]thiazolo[5,4-c]rifamycin SV

I claim:

1. A compound of the formula:

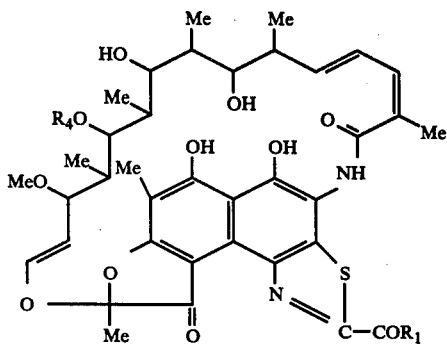

wherein: $R_1$ represents loweralkoxy, cycloalkoxy having from 5 to 8 carbon atoms in the ring, phenoxy, benzoxy, or an amino or hydrazino moiety represented by the formulas: $-NR_2R_3$ and $-NH-NR_2R_3$, respectively, wherein $R_2$ and $R_3$ are independently selected from the group consisting of hydrogen, lower alkyl hydroxy lower alkyl, cycloalkyl having from 5 to 8 carbon atoms in the ring, phenyl or benzyl or $R_2$ and $R_3$ taken together with the adjacent nitrogen atom represent a saturated 5 or 6 membered heterocyclic ring which may contain an additional nitrogen or oxygen atom in the ring thereby forming a residue of pyrrolidino, piperidino, piperazino, N-lower alkylpiperazino or morpholino and $R_4$ represents hydrogen or acetyl.

2. A process for preparing a 4-desoxy-thiazolo[5,4-c]rifamycin SV of the formula:

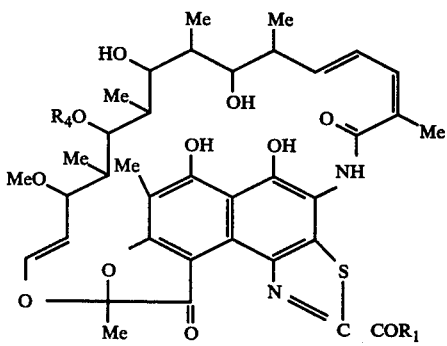

$R_1$ represents loweralkoxy, cycloalkoxy having from 5 to 8 carbon atoms in the ring, phenoxy, benzoxy, or an amino or hydrazino moiety represented by the formulas: $-NR_2R_3$ and $-NH-NR_2R_3$, respectively, wherein $R_2$ and $R_3$ are independently selected from the group consisting of hydrogen, lower alkyl, hydroxy lower alkyl, cycloalkyl having from 5 to 8 carbon atoms in the ring, phenyl or benzyl or $R_2$ and $R_3$ taken together with the adjacent nitrogen atom represent a saturated 5 or 6 membered heterocyclic ring which may contain an additional nitrogen or oxygen atom in the ring thereby forming a residue of pyrrolidino, piperidino, piperazino, N-lower alkylpiperazino or morpholino and $R_4$ represents hydrogen or acetyl; which comprises reacting rifamycin S or 25-deacetyl rifamycin S with a cysteine having the formula:

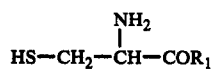

wherein $R_1$ is as defined above, whereby a 3-(2-substituted ethylthio)-rifamycin SV of the formula:

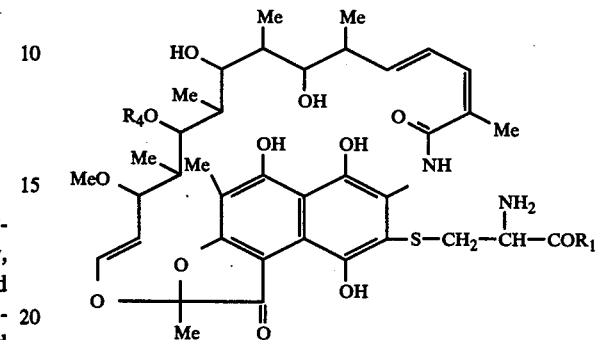

is obtained, wherein $R_1$ and $R_4$ are as defined before, and contacting said 3-(2-substituted ethylthio)-rifamycin SV with an oxidizing agent in an aqueous buffered water-miscible solvent system at a controlled pH of between 2 and 6.5.

3. The process of claim 2 wherein the reaction between the rifamycin S or 25-desacetyl rifamycin S and the cysteine derivative is carried out in a water-miscible organic solvent at a temperature between room temperature and the boiling temperature of the reaction mixture.

4. The process of claim 2 wherein the oxidizing agent is selected from the group consisting of quinones, organic nitrites, peroxides, persulfates, nitrous acid, tetravalent manganese and lead derivatives, trivalent iron derivatives, mercuric and cupric salts.

5. The process of claim 2 wherein the controlled pH is between 4.2 and 4.8.

6. The process of claim 2 wherein the reaction between the rifamycin S or 25-desacetyl rifamycin S and the cysteine and the subsequent contacting of the obtained 3-(2-substituted ethylthio)-rifamycin SV with an oxidizing agent are performed in a single operation.

7. The process of claim 2 wherein $R_1$ of the 4-desoxy-thiazolo(5,4-c)rifamycin SV is an alkoxy further including the step of transforming said 4-desoxy-thiazolo(5,4-c)rifamycin into a second 4-desoxy-thiazolo(5,4-c)rifamycin, wherein $R_1$ represents an amino or hydrazino moiety represented by the formulas: $-NR_2R_3$ and $-NH-NR_2R_3$ by reacting the first derivative with a corresponding amine or hydrazine of the formula $HNR_2R_3$ or $H_2N-NR_2R_3$ respectively.

8. The process of claim 3 wherein the solvent is selected from the group consisting of lower alkanol, dioxane and tetrahydrofuran.

9. The process of claim 4 wherein the oxidizing agent is selected from p-quinone, 2,5-dimethyl-p-quinone, 2,6-dimethoxy-p-quinone, tetrachloro-p-quinone, dichlorodicyano-p-quinone, duroquinone, rifamycin S, alkyl nitrites, hydrogen peroxide, alkali metal persulfates, alkali metal ferricyanides, cupric acetate, mercuric acetate and manganese dioxide.

10. The process of claim 6 wherein the rifamycin S 25-desacetyl rifamycin S and the cysteine are reacted in the presence of an oxidizing agent selected from tetrasubstituted quinones and rifamycin S at a controlled pH between 4.2 and 4.8.

* * * * *

UNITED STATES PATENT AND TRADEMARK OFFICE
CERTIFICATE OF CORRECTION

PATENT NO. : 4,129,562
DATED : December 12, 1978
INVENTOR(S) : Renato Cricchio

It is certified that error appears in the above—identified patent and that said Letters Patent are hereby corrected as shown below:

Column 9, line 21, "lower alkyl" should read -- lower alkyl, --

Column 10, line 36, "trivalentiron" should read -- trivalent iron --

Signed and Sealed this

Twelfth Day of June 1979

[SEAL]

Attest:

RUTH C. MASON
Attesting Officer

DONALD W. BANNER
Commissioner of Patents and Trademarks